United States Patent [19]

Munk

[11] Patent Number: 4,735,569
[45] Date of Patent: Apr. 5, 1988

[54] ORTHODONTIC APPLIANCE AND METHOD OF PREPARATION THEREOF

[76] Inventor: Charles F. Munk, 5825 S. Main St., Clarkston, Mich. 48016

[21] Appl. No.: 847,936

[22] Filed: Apr. 3, 1986

[51] Int. Cl.⁴ ................................................ A61C 3/00
[52] U.S. Cl. .......................................... 433/9; 433/8; 433/213
[58] Field of Search ..................... 433/9, 8, 2, 180, 213

[56] References Cited

U.S. PATENT DOCUMENTS

| | | | |
|---|---|---|---|
| 2,889,625 | 6/1959 | Saffir | 433/180 |
| 3,797,115 | 3/1974 | Silverman et al. | 433/9 |
| 4,068,379 | 1/1978 | Miller et al. | 433/9 |
| 4,216,583 | 8/1980 | Reynolds | 433/9 |
| 4,470,809 | 9/1984 | Klepacki | 433/9 |

Primary Examiner—John J. Wilson
Attorney, Agent, or Firm—Remy J. VanOphem

[57] ABSTRACT

An aesthetically pleasing orthodontic appliance which is formed by casting a molten precious metal alloy, a major portion of which is gold and a minor portion of which is platinum, such appliance having a contoured, tooth-engaging surface with at least one irregularity therein to permit a dental adhesive to form a mechanical bond with the appliance, the irregularity being a recess which extends into the interior of the appliance to reduce the weight thereof, and a "lost wax" type of process for forming such a precious metal alloy orthodontic appliance using an organic orthodontic appliance as a form, the contoured, tooth-engaging rear surface of such organic orthodontic appliance being treated to form at least one irregularity therein corresponding to the irregularity that is desired in the precious metal alloy orthodontic appliance.

10 Claims, 2 Drawing Sheets

ORTHODONTIC APPLIANCE AND METHOD OF PREPARATION THEREOF

BACKGROUND OF THE INVENTION

1. Field of the Invention

This invention relates to an orthodontic appliance which is made from an alloy of gold and platinum or other precious metal of suitable luster and hardness, and to a method for preparing such an orthodontic retainer.

2. Description of the Prior Art

Gold alloys and other precious metal alloys are widely used in restorative dentistry, for example, as fillings, crowns and bridges. In such applications, the precious metal alloy that is used in any such restorative dental device is selected basically for its functional characteristics, such as durability and compatibility with the interior portion of a tooth to which it is attached and, in any such application, the precious metal alloy dental device is generally not readily visible from a position away from the wearer. Hence, the visual characteristics of a restorative device formed from a precious metal alloy do not have much significance in the selection of the metal alloy that is used in the device.

In orthodontics, however, various types of devices, such as brackets and retainers, are affixed to the front surfaces of the teeth being treated and, especially in the case of front teeth, both upper and lower, these devices are quite visible to someone who is near to the user and who is looking toward the user when the mouth of the user is open. Nevertheless, such orthodontic brackets and retainers have heretofore been formed from materials which lack the aesthetic qualities of precious metals, including such non-metallic materials as acrylic plastic, as is disclosed in U.S. Pat. No. 3,345,745 (G. Muller) and in U.S. Pat. No. 3,303,565 (G. V. Newman), and non-precious metals, such as stainless steel, as is disclosed in U.S. Pat. No. 4,100,678 (K. Yatabe) and in U.S. Pat. No. 4,165,561 (F. R. Miller, et al). Ceramics, such as aluminum oxide, as is disclosed in U.S. Pat. No. 4,216,583 (J. M. Reynolds), have also been used for such purposes. One of the problems that must be overcome with respect to the use of precious metal alloys in the manufacture of orthodontic appliances is that such precious metal alloys have greater weight than their prior art counterparts, due to the high densities of such precious metal alloys. Thus, there is a problem of movement or drift of the orthodontic appliances on the tooth, due to gravity, while the adhesive that is used to bond the orthodontic appliance is curing or setting, since the tooth surface to which the appliance is being bonded is usually oriented in a substantially vertical direction. Additionally, due to the relative chemical inertness of such a precious metal alloy, their use in orthodontic devices involves a problem that was not encountered in organic orthodontic devices, such as acrylic brackets and retainers, namely the problem that there is no appreciable chemical bonding of the dental adhesive to the precious metal dental device. Thus, the bonding of the dental adhesive to the precious metal orthodontic device must be almost entirely physical or mechanical in nature.

SUMMARY OF THE INVENTION

According to the present invention, there is provided a precious metal alloy orthodontic device, such as a bracket or a retainer, which has improved aesthetic characteristics, relative to prior art orthodontic devices, and which has novel physical characteristics to overcome the problems which arise in the bonding of such a precious metal alloy orthodontic device to a tooth because of the physical characteristics of precious metal alloys relative to other materials that are used in prior art orthodontic devices, namely the increased density and decreased chemical adhesion of such precious metal alloys. There is also provided a method for the manufacture of such a precious metal alloy orthodontic device.

A precious metal alloy orthodontic device according to the present invention has a substantially extended tooth engaging rear surface to physically trap the dental adhesive that is used to bond such device to a tooth of a patient to be fitted with such device, to thereby enhance the physical bonding of such device to the tooth as a way of offsetting the reduced chemical bonding that takes place between the device, the adhesive and the tooth as a result of the chemical inertness of the precious metal alloy that is used in the device. Preferably, the surface extension of the rear surface of the device is provided at least in part in the form of a recess extending into the interior portion of the device, to thereby lightweight the device and reduce its tendency to move or drift on the tooth, after application to the tooth and before the setting or curing of the adhesive that is used to effect such application, such movement or drifting otherwise being more serious in the case of a precious metal alloy orthodontic device than in the case of its prior art counterparts due to the high density of precious metal alloys.

In the method of the present invention, an acrylic or other organic prior art orthodontic device is suitably treated to extend the area of its rear tooth engaging surface, for example, by drilling an annular recess or other recess therein, by etching or by the bonding of beads thereto, and the then treated prior art orthodontic device is used as a form to produce a precious metal alloy orthodontic device of essentially identical dimensional characteristics by casting in a process similar to the "lost wax" process. The precious metal alloy orthodontic device of the present invention has improved aesthetic characteristics relative to the acrylic or other orthodontic device which it replaces and, due to the extension of its rear tooth engaging surface, it may be bonded to a tooth by a suitable dental adhesive principally by physical bonding.

Accordingly, it is an object of the present invention to provide a suitable orthodontic device that is formed from a precious metal alloy.

It is a further object of the present invention to provide a method of forming a precious metal alloy dental device.

For a further understanding of the present invention and the objects thereof, attention is directed to the drawing and the following description thereof, to the detailed description of the preferred embodiment of the invention, and to the appended claims.

DETAILED DESCRIPTION OF THE PREFERRED EMBODIMENT

Figure 1:
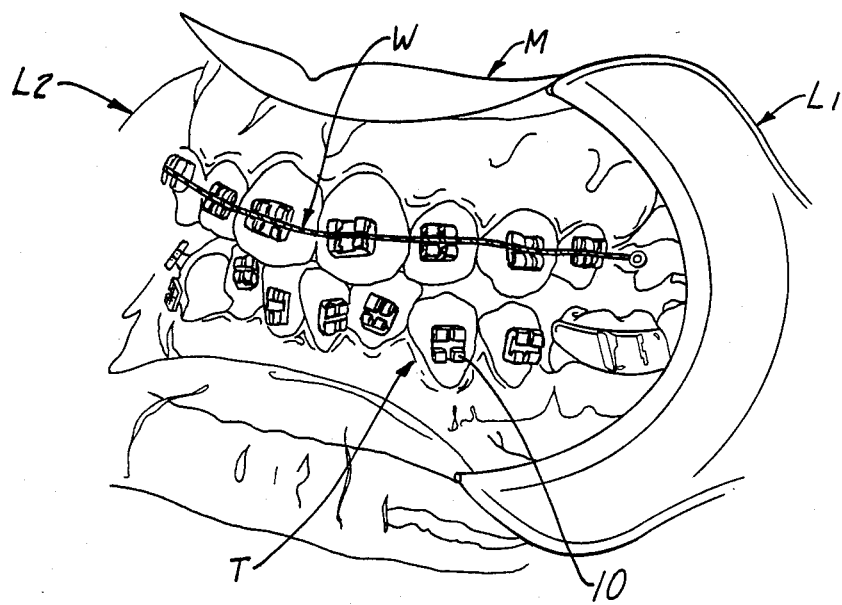
FIG. 1 is a perspective view of the mouth of a dental patient that is being fitted with orthodontic devices according to the present invention.

FIG. 1 illustrates the open mouth M of a dental patient, the open mouth M being held open by lip retractors L1 and L2 on opposite sides of the mouth M. As is clear from FIG. 1, the teeth, such as the lower tooth T, are in the process of being fitted with orthodontic appliances, such as the bracket 10 that is affixed to the tooth T, the upper teeth in the mouth M also having brackets affixed thereto with a tensioning wire W attached to the brackets that are affixed to the upper teeth in the mouth M. Upon the completion of the attachment of the bracket 10 to the tooth T, another tensioning wire, not shown, will be attached to such lower teeth brackets. Each such bracket, such as the bracket 10, has a contoured, tooth engaging rear surface, and a suitable dental adhesive, such as an FDA approved acrylic dental adhesive, is used to adhesively bond each such bracket to the tooth to which it is affixed. As thus far described, the orthodontic procedure depicted in FIG. 1, including the use of various types of non-precious metal alloy orthodontic brackets and various types of tensioning wires, is conventional.

As is also quite clear from FIG. 1, the various brackets which are affixed to the teeth in the mouth M are quite visible to someone who is standing near the dental patient whose mouth M is shown in FIG. 1, especially when the mouth M is open. Such brackets can be quite unsightly, especially when such brackets are formed from a material which has little original luster or which loses its luster during service due to staining or tarnishing, an event which can easily occur in the environment of a human mouth, especially over the prolonged duration of the attachment of such brackets to their respective teeth as is typical in orthodontic treatment, for example, over a period of several months to a few years.

According to the present invention, therefore, the appearance of the bracket 10 and the other brackets shown in the mouth M is enhanced by forming or preparing such brackets from an alloy of a precious metal, for example, a gold-platinum alloy of suitable hardness. Such alloys possess an attractive, lustrous appearance, which accounts for the extensive use of materials in this class in jewelry, and such materials are quite inert in a chemical sense, which enhances their resistance to staining or tarnishing in use. However, the types of precious metal alloys that are used in jewelry are usually too soft to withstand the loads that can be imposed on brackets formed therefrom during a prolonged period of orthodontic treatment, such loads being imposed on a continuous basis by the tension in the tensioning wire W that is attached to such brackets, and such loads further being imposed on such brackets on an intermittent basis as the dental patient chews on hard or chewey foods during the course of the orthodontic treatment. Hence, it is important that the precious metal alloy that is used in the orthodontic bracket 10 and the other brackets shown in the mouth M be considerably harder than the typical jewelry precious metal alloy and that it have good chemical durability for corrosion resistance in a human mouth. Preferably for good color and corrosion resistance, it should have a gold content of at least 18 karat and it should have some platinum content for good hardness. An alloy which has been found to be quite satisfactory for use in forming precious metal alloy orthodontic brackets and other orthodontic appliances including retainers by casting is an 18 karat gold platinum palladium-silver casting gold alloy that is available from Jelenko Dental Health Products in Armoutz, N.Y. under the product designation "Jelenko No. 7" ®. Such an alloy has a rated ultimate tensile strength (quenched) of 71,000 lbs/in$^2$ (4993 kg/cm$^2$). Another suitable precious metal alloy has been found to be Jelenko's 17 karat gold-platinum casting alloy "JEL-4" ® which has a rated Brinnett Hardness of 150 (quenched) and a rated ultimate tensile strength (quenched) of 66,000 lbs/in$^2$ (4641 kg/cm$^2$). These materials are now being sold for use in various types of restorative dental devices, such as hard inlays, thin crowns, fixed bridgework and partial dentures, but have not heretofore been sold for use in orthodontic brackets and other orthodontic appliances.

Figure 8:
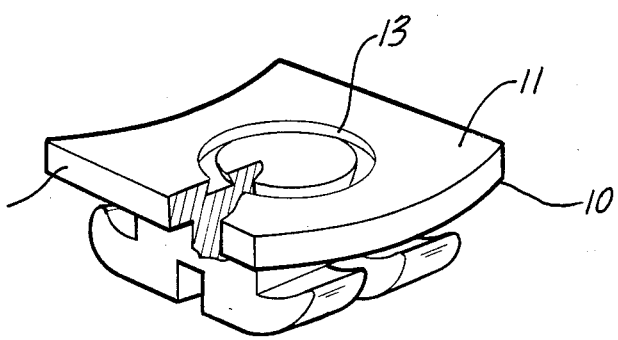
FIG. 8 is a perspective view of an orthodontic device according to the present invention, which device was produced by the method of FIGS. 4 through 7 with a portion of such orthodontic device being broken away to better illustrate a feature of such orthodontic device.

As is shown in FIG. 8, in the preferred embodiment of a precious metal alloy orthodontic bracket 10 according to the present invention, such orthodontic bracket 10 has a contoured, tooth-engaging rear surface 11, which is adapted to be bonded to a tooth, not shown, by means of a suitable adhesive, also not shown. To assist in the bonding of the orthodontic bracket 10 to a tooth, the contour of the tooth-engaging rear surface 11 generally corresponds to the contour of the exterior of the tooth to which it is to be bonded. However, because of the resistance of the precious metal alloy in the orthodontic bracket 10 to chemical bonding as a result of the chemical inertness of the precious metal alloy, it is necessary to extend the tooth-engaging rear surface 11 by providing surface irregularities therein so that the dental adhesive will be physically trapped in the irregularities in such surface to assist in the physical bonding of the orthodontic bracket to an associated tooth. Such extension of the tooth-engaging rear surface 11 of the orthodontic bracket, as is shown in FIG. 8, preferably involves the forming of a blind recess in a core portion 12 of the orthodontic bracket 10, such as an annular recess 13 which is formed in the tooth-engaging rear surface 11 of the orthodontic bracket 10. To assist in the retaining of adhesive in the annular recess 13 of the orthodontic bracket 10, the annular recess 13 preferably is formed with a dovetail configuration, that is with a radial thickness at the bottom or blind end thereof that is greater than the radial thickness of the annular recess 13 on the tooth-engaging rear surface 11 of the orthodontic bracket 10.

In providing extension to or irregularities to the tooth-engaging rear surface 11 of the orthodontic bracket 10, such as by providing the annular recess 13 extending into the core portion 12 from the tooth-engaging rear surface 11 thereof, the weight of the orthodontic bracket 10 is reduced, and there is less tendency for the orthodontic bracket 10 to move or drift on the tooth to which it is being applied while the dental adhesive is curing or setting. Preferably, at least approximately 20% of the volume of the orthodontic bracket 10 is represented by the volume of the annular recess 13. This will reduce the weight of a precious metal alloy orthodontic bracket 10 to approximately that of a comparable prior art stainless steel bracket without such a recess, notwithstanding that precious metal alloys are approximately 20% more dense than stainless steel.

Figure 2:
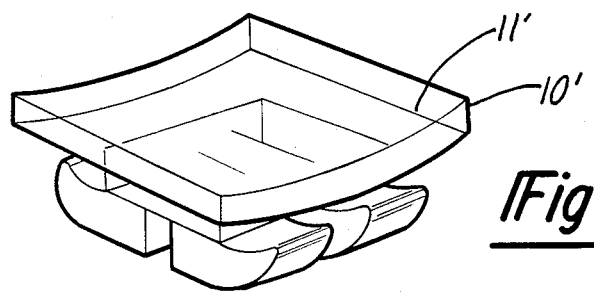
FIG. 2 is a perspective view of a prior art orthodontic device that is adapted to be used in the practice of the method of the present invention.
Figure 3:
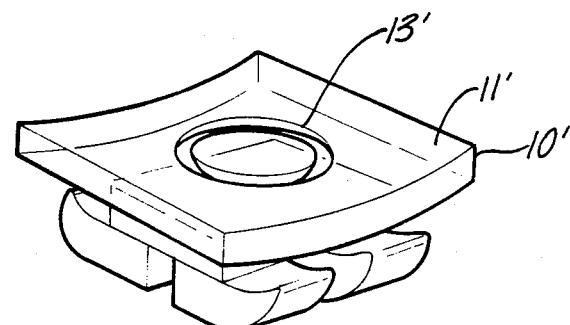
FIG. 3 is a perspective view of the orthodontic device of FIG. 2 after the treatment of such orthodontic device to permit it to be used in the method of the present invention.
Figure 4:
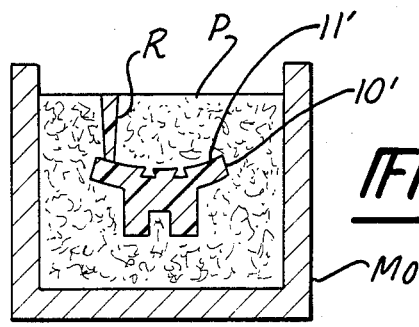
FIGS. 4 through 7 are schematic illustrations of a series of steps in the method of the present invention for preparing an orthodontic device.

A method for the preparation of a precious metal alloy orthodontic bracket 10 begins with a standard, commercially available molded orthodontic bracket 10', as shown in FIG. 2, which orthodontic bracket 10' is formed from an organic material, such as an acrylic resin. The orthodontic bracket 10' has a smooth, contoured, tooth-engaging rear surface 11', and the method begins with the treatment of the rear surface 11' to form an annular reces 13' therein, as is shown in FIG. 3. The annular recess 13' can be formed, for example, by the use of a small burnishing tool in a dental drill and, when working with a clear plastic orthodontic bracket 10', such as an acrylic resin bracket, it is useful, for purposes of visibility, to apply a food grade colorant to the tooth-engaging rear surface 11' prior to forming the annular recess 13' therein.

Figure 5:
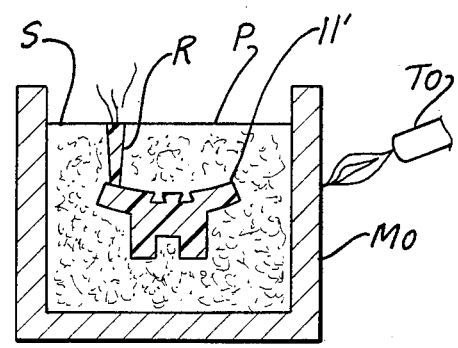
Figure 6:
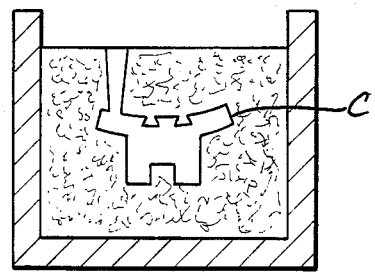

After the treatment of the rear surface 11' of the orthodontic bracket 10', as heretofore described, the treated orthodontic bracket is inserted into a potting material P, such as plaster of Paris in a mold MO, an acrylic resin or similar riser R preferably being attached to the rear surface 11' of the orthodontic bracket 10 before it is inserted into the potting material P to extend from the rear surface 11' of the orthodontic bracket 10' at least to the top surface S of the potting material P. Thereafter, as is shown in FIG. 5, the mold MO is heated, for example, by a propane-oxygen torch TO, or in an oven, to a temperature of approximately 1000° F. and for a duration of approximately 80 minutes to cure the potting material P and to liquify, and partially gasify the treated orthodontic bracket 10' and associated riser R until it disappears entirely, leaving a cavity C in the potting material that will accurately correspond to the outline of the original treated orthodontic bracket 10' with associated riser R. The cavity C is shown in FIG. 6.

To the extent that any of the material in the treated orthodontic bracket 10' evaporates, it can escape from the cavity C in the mold MO through the portion of the cavity C that was originally occupied by the riser R, this portion of the cavity C serving as a sprue. The process as described for forming a cavity in a mold is similar to that which has been used in forming mold cavities for various other products by a process which is sometimes referred to as the "lost wax process".

Figure 7:
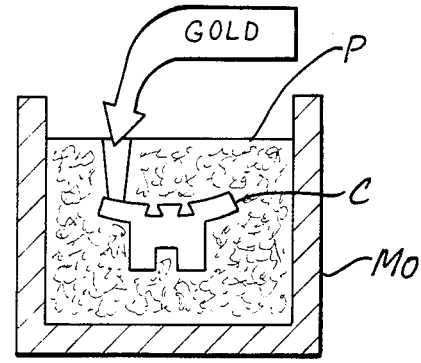

After the cavity C has been formed in the potting material P in the mold MO, as heretofore described, a suitable molten precious metal alloy is poured into the cavity C through the portion thereof that was originally occupied by the riser R, as is generally indicated in FIG. 7. Preferably, for alloys of the type heretofore described, the molten precious metal alloy is at a temperature of approximately 1850° F. when it is poured into the cavity C. The molten precious metal alloy is then slowly cooled, preferably by bench cooling, to solidify to the shape of the portion of the cavity C that was formed from the treated orthodontic bracket 10' to form the precious metal alloy orthodontic bracket 10 whose exterior dimensions will correspond very closely to those of the treated orthodontic bracket 10'. The slow cooling of the molten precious metal alloy, as opposed to forced or accelerated cooling thereof, will result in somewhat greater hardness, which is a desirable attribute for a load bearing precious metal alloy product, such as a precious metal alloy orthodontic appliance.

In affixing an orthodontic bracket 10 to a tooth, it is important that the dental adhesive be pressed into the annular recess 13, as opposed to allowing it to just flow thereinto during a coating or painting of the rear surface 11, to insure a good mechanical or physical bond between the adhesive and the undercut portions of the annular recess 13.

While not specifically illustrated herein, it is contemplated that other techniques may be employed in the treatment of the smooth, contoured, tooth-engaging rear surface 11 of an organic orthodontic bracket 10' to extend the area of such surface or to add irregularities thereto, before such treated orthodontic bracket 10' is used as a form in the molding of a precious metal alloy orthodontic bracket 10. For example, such tooth-engaging surface can be roughened mechanically by abrading or sanding or by chemically etching or it can be extended by the bonding of small organic beads or a screen thereto. These techniques do not, however, provide for a comparable lightweighting of the finished precious metal alloy orthodontic bracket as that which is obtained by the forming of a recess, such as the annular recess 13', into the organic orthodontic bracket 10'.

Although the best mode contemplated by the inventor for carrying out the present invention as of the filing date hereof has been shown and described herein, it will be apparent to those skilled in the art that suitable modifications, variations, and equivalents may be made without departing from the scope of the invention, such scope being limited solely by the terms of the following claims.

What is claimed is:

1. An aesthetically pleasing orthodontic appliance having a contoured, tooth-engaging surface, said orthodontic appliance being formed from a precious metal alloy, said precious metal alloy having good corrosion resistance and good hardness, said orthodontic appliance being adapted to being bonded to a tooth by the application of a dental adhesive to said contoured, tooth-engaging surface, said contoured, tooth-engaging surface having at least one irregularity therein to permit said dental adhesive to form a mechanical bond to said orthodontic appliance, said at least one irregularity comprising an annular recess extending into said orthodontic appliance from said contoured, tooth-engaging surface.

2. An orthodontic appliance according to claim 1 wherein a major portion of said precious metal alloy comprises a gold and a minor portion of said precious metal alloy comprises a platinum.

3. An orthodontic appliance according to claim 2 wherein said orthodontic appliance is formed by casting said precious metal alloy when said precious metal alloy is in a liquid state.

4. An orthodontic appliance to claim 1 wherein said annular recess has a blind end away from said contoured, tooth-engaging surface, wherein said annular recess has a first radial thickness at said contoured, tooth-engaging surface and a second radial thickness at said blind end and wherein said second radial thickness is greater than said first radial thickness.

5. A method for forming an aesthetically pleasing precious metal alloy orthodontic appliance having a contoured, tooth-engaging surface with at least one irregularity therein, said method comprising the steps of:
- providing an organic form having a smooth, contoured, tooth-engaging surface;
- treating said smooth, contoured, tooth-engaging surface to form an annular recess therein;
- providing a mold having a potting material therein;
- immersing said organic form in said potting material in said mold;
- heating said mold to cause said organic form to dissolve into said potting material or to evaporate to thereby form a cavity in said potting material, said cavity having the outline of said organic form;
- pouring molten precious metal alloy into said cavity; and
- cooling said molten precious metal alloy to solidify said precious metal alloy into said precious metal alloy orthodontic appliance.

6. A method according to claim 5 wherein said step of treating said smooth, contoured, tooth-engaging surface to form an annular recess in said smooth contoured, tooth-engaging surface of said organic orthodontic appliance involves forming said annular recess with a blind end away from said contoured, tooth-engaging surface of said organic orthodontic appliance, said annular recess having a first radial thickness at said blind end and a second radial thickness at said contoured, tooth-engaging surface, said first radial thickness being greater than said second radial thickness.

7. A method according to claim 5 wherein said mold is heated to a temperature of at least approximately 1000° F. for a duration of at least approximately 80 minutes.

8. A method according to claim 5 wherein a major portion of said molten precious metal alloy comprises gold and a minor portion of said molten precious metal alloy comprises platinum.

9. A method according to claim 8 wherein said molten precious metal alloy is at a temperature of at least approximately 1850° F. when it is poured into said cavity.

10. A method according to claim 9 wherein said molten precious metal alloy is cooled slowly by bench cooling.

* * * * *

UNITED STATES PATENT AND TRADEMARK OFFICE
CERTIFICATE OF CORRECTION

PATENT NO. : 4,735,569
DATED : April 5, 1988
INVENTOR(S) : Charles F. Munk

It is certified that error appears in the above-identified patent and that said Letters Patent is hereby corrected as shown below:

Column 5, line 35, delete "1000°F." and insert ---- 1000°F ----.

Column 5, line 60, delete "1850°F." and insert ---- 1850°F ----.

In the Claims

Column 6, line 55, delete "a".

Column 6, line 60, after "appliance" insert ---- according ----.

Column 8, line 10, delete "1000°F." and insert ---- 1000°F ----.

Column 8, line 18, delete "1850°F." and insert ---- 1850°F ----.

Signed and Sealed this

First Day of November, 1988

Attest:

DONALD J. QUIGG

Attesting Officer

Commissioner of Patents and Trademarks